United States Patent
Gold et al.

(10) Patent No.: US 7,079,244 B2
(45) Date of Patent: Jul. 18, 2006

(54) PARTICLE ANALYZER WITH SPECIMEN TUBE IN-LINE MIXER

(75) Inventors: Kenneth S. Gold, Bell Canyon, CA (US); John P. Pelmulder, Chatsworth, CA (US); Richard H. Turner, Mercer Island, WA (US)

(73) Assignee: International Remote Imaging Systems, Inc., Chatsworth, CA (US)

( * ) Notice: Subject to any disclaimer, the term of this patent is extended or adjusted under 35 U.S.C. 154(b) by 264 days.

(21) Appl. No.: 10/696,924

(22) Filed: Oct. 29, 2003

(65) Prior Publication Data

US 2004/0109386 A1    Jun. 10, 2004

Related U.S. Application Data

(60) Provisional application No. 60/427,469, filed on Nov. 18, 2002, provisional application No. 60/427,624, filed on Nov. 18, 2002.

(51) Int. Cl.
*G01N 15/02*    (2006.01)

(52) U.S. Cl. .................................................... 356/338

(58) Field of Classification Search ...................... None
See application file for complete search history.

(56) References Cited

U.S. PATENT DOCUMENTS

| 4,338,024 A | | 7/1982 | Bolz et al. |
| 4,393,466 A | | 7/1983 | Deindoerfer et al. |
| 4,530,466 A | | 7/1985 | Rounkles et al. |
| 5,607,233 A | * | 3/1997 | Yant et al. ................... 366/102 |
| 5,674,032 A | * | 10/1997 | Slocum et al. ............... 409/131 |
| 6,262,131 B1 | | 7/2001 | Arcuri et al. |
| 6,585,407 B1 | * | 7/2003 | Koch .......................... 366/336 |
| 6,608,680 B1 | | 8/2003 | Basiji et al. |
| 6,755,079 B1 | | 6/2004 | Proett et al. |

FOREIGN PATENT DOCUMENTS

WO    WO 96/05909    2/1996

OTHER PUBLICATIONS

Blevins, Robert D., Applied Fluid Dynamics Handbook, Published 1984 by Van Nostrand Reinhold Co., Inc., pp. 54-71.

Růžička, Jaromir et al., Flow Injection Analysis, second edition, Published 1988 by John Wiley & Sons, Inc., pp. 105-117.

* cited by examiner

*Primary Examiner*—Tu T. Nguyen

(57) ABSTRACT

A particle analyzer that includes a specimen source, a flow cell, a pump and delivery tube for transporting specimen fluid from the specimen source to the flow cell, a dispensing valve for injecting stain from a stain source into the specimen fluid in the delivery tube, and a mixing device for mixing the stain and the specimen fluid together. The mixing device includes a cylindrical shaped member having an outer surface, a channel formed in the outer surface with the channel including circumferential and longitudinal turns, and a hollow mixing tube disposed in the channel. As the stain and the specimen fluid flow through the mixing tube, they travel through the circumferential and longitudinal turns and are mixed together. A fluid sensor employing a sensor RC circuit and a reference RC circuit detects capacitance changes in the delivery tube for detecting the presence or absence of fluid therein.

47 Claims, 4 Drawing Sheets

PARTICLE ANALYZER WITH SPECIMEN TUBE IN-LINE MIXER

This application claims the benefit of U.S. Provisional Application No. 60/427,469, filed Nov. 18, 2002, and of U.S. Provisional Application No. 60/427,624, filed Nov. 18, 2002.

FIELD OF THE INVENTION

The present invention relates to methods and systems for analyzing particles in a dilute fluid sample, and more particularly to mixers and detectors that operate on the flow of specimen fluid "on the fly".

BACKGROUND OF THE INVENTION

Methods and systems for analyzing particles and particularly sediments are well known in the art, as disclosed in U.S. Pat. Nos. 4,338,024 and 4,393,466, which are incorporated herein by reference. Such systems utilize a flow cell through which fluid samples (specimens) are passed, and a particle analyzer for capturing still frame images of the fluid passing through the flow cell. Thus, the flow cell positions and presents the sample fluid containing particles of interest for analysis. The more accurately that the sample fluid is positioned by flow cell, the better the analysis of the particles therein that can be made.

Typical flow cells cause the sample fluid, and a sheath fluid that buffers the sample fluid, to flow together from a large entry chamber into a small cross sectional examination area or region. The transition from the inlet or entry chambers to the examination region forms a hydrodynamic lens that squeezes both the sample fluid and the sheath fluid proportionally into the smaller space. Where the particles of interest are microscopic particles, the resulting cross-sectional space occupied by the sample fluid must be positioned within the depth of field of the analyzer, such as an optical system or a laser system, to obtain the best analytical information. For the best hydrodynamic focus, a large area of sheath flow must envelop the small area of sample fluid without any swirling or vortices. Thus, uniform flow of sample and sheath fluids through the flow cell is essential for optimal operation of particle analyzers.

Particle analyzer devices, such as those referenced above, often stain the sample fluid before it goes through the flow cell for image capture. The stain is a highly concentrated liquid, and it has been determined that the staining process requires a sample-to-stain ratio of approximately 166:1. Using a separate mixing chamber (e.g. with a spinning mixing bar) is not ideal because it delays the amount of time it takes to get the stained sample fluid to the flow cell, it increases the required amount of sample fluid, and it adds an additional component that can be difficult to wash or rinse between samples. In line mixers have also been used, such as helically coiled tubes, randomly-coiled tubes (also called "3D" and in some situations "knitted" tubes), zig-zag tubes with "sharp" corners, and ball-mixers (i.e. a string of small spheres in the flow stream). The more complex the in-line mixing path, the more efficient the mixing, but also the more difficult it is to manufacture and to clean between uses. Particle analyzer devices have a no-carryover requirement, where old samples must be thoroughly washed or rinsed away before a new sample is collected and analyzed. The more "corners" in a mixer, the more likely it is for the mixing device to accumulate debris (e.g. from old samples) and the more difficult it is to clean the mixer in-between samples. Some of these mixers require excessive amounts of the sample to efficiently operate. Lastly, some of these mixing devices introduce a significant pressure drop, which makes it difficult to provide the sample to the flow cell with the proper pressure and flow rate.

Reducing the amount of sample fluid that needs to be aspirated from the collection point can be accomplished by reducing the inner diameter (ID) of the delivery tubing used to carry the sample to the flow cell, and keeping any fluid mixer as small as possible. However, automated particle analyzers also need to detect whether or not fluid is flowing (i.e. is present) in the delivery tubing. A delivery tube with a 0.033 inch ID requires a satisfactory volume of sample, but the amount of fluid that represents presence of the liquid is only about 5 µL per centimeter of the tubing. One challenge then is performing fluid sensing in such small tubing, without requiring any additional tube length to provide for the fluid sensing, and without disturbing the flow of fluid that could adversely affect stain mixing and flow cell operation.

It is well known that the dielectric constant of water and solutions involving water is very high compared to that of air. Water below 55° C. has a dielectric constant from 70 to 88, while air is 1.00. For sensing the small amounts of water consistent with small tubes, capacitance-sensing electrodes external to the tube can be used. However, without extending the length of the tube, those electrodes will be quite small. With small electrodes (about 1 cm long), the capacitive difference between water in the tube and no water in the tube is typically less than 1 pF, which can be difficult to detect.

There are many capacitance sensors presently available that can work down to the picoFarad level, but the stability of their measuring process is not precise enough to allow unattended operation for very long before the measured threshold drifts beyond usable levels. To counteract this drift, some devices use a "continuous calibration" technique, but that presupposes an assumed format for the presence or absence of liquid in the tube. For example, Q-Prox (of Southampton, England) has a 6-channel capacitance-based push-button sensor IC chip. While this sensor apparently senses just a few pF of capacitance change, it requires an elaborate self-adjusting system of "calibrating" the sensor points so that the drift in the IC can be compensated away. This scheme assumes the absence of any user supplied liquid, and uses this assumption to allow its self-calibration. Such a scheme would not work well for a liquid sensing scheme where the presence of the liquid could be true or false without a known time-varying schedule.

There is a need for a fluid mixer that mixes with the smallest volume possible to minimize the amount of sample fluid that must be involved in the mixing process, where the mixing is performed in the shortest length possible to minimize the transit time along the mixing path. Such a mixer should not contain any places to "store contaminants, so that it is easy to clean after the sample fluid has passed through, and it needs to be easy to manufacture at a low cost. A sensitive but reliable liquid sensor is also needed, one that works with small diameter tubing and is compatible with the fluid sensor and flow cell operation.

SUMMARY OF THE INVENTION

The present invention is an in-line fluid mixer, an in-line fluid sensor, and a particle analyzer incorporating the same, that reliably mix and detect small amounts of fluid traveling through small diameter tubing.

A fluid mixing device for mixing a fluid with a fluid kinematic viscosity v includes a core member having an outer surface and a longitudinal axis, and a channel formed in the outer surface for receiving the fluid, wherein the channel includes at least one radial mixing turn and a plurality of axial mixing turns through which the fluid flows, wherein the fluid flowing through the channel is mixed by the radial and axial mixing turns.

In another aspect of the present invention, a particle analyzer includes a source of specimen fluid, a flow cell, a mixing device, and a pump. The mixing device includes a core member having an outer surface and a longitudinal axis, and a channel formed in the outer surface having at least one radial mixing turn and a plurality of axial mixing turns. The pump pumps the specimen fluid from the specimen fluid source, through the mixing device wherein the specimen fluid flowing through the channel undergoes mixing by the radial and axial mixing turns, and then to the flow cell.

In yet another aspect of the present invention, a fluid mixing device for mixing a fluid having a fluid kinematic viscosity v includes a hollow mixing tube disposed about a longitudinal axis for receiving the fluid, wherein the mixing tube forms a fluid path having at least one radial mixing turn and a plurality of axial mixing turns through which the fluid flows. The fluid flowing through the fluid path is mixed by the radial and axial mixing turns.

In yet one more aspect of the present invention, a sensor for detecting the presence of fluid in a hollow tube includes first and second sensor circuits. The first sensor circuit includes an input for receiving an oscillating signal, an output, and a capacitor, wherein the first capacitor includes first and second electrodes, and wherein a portion of the hollow tube extends between the first and second electrodes. The second sensor circuit has an input for receiving the oscillating signal, an output, and a reference capacitor. A voltage difference between the first sensor circuit output and the second sensor circuit output varies depending upon the presence or absence of fluid in the portion of the hollow tube between the first and second electrodes.

Other objects and features of the present invention will become apparent by a review of the specification, claims and appended figures.

DETAILED DESCRIPTION OF THE PREFERRED EMBODIMENTS

Figure 1:
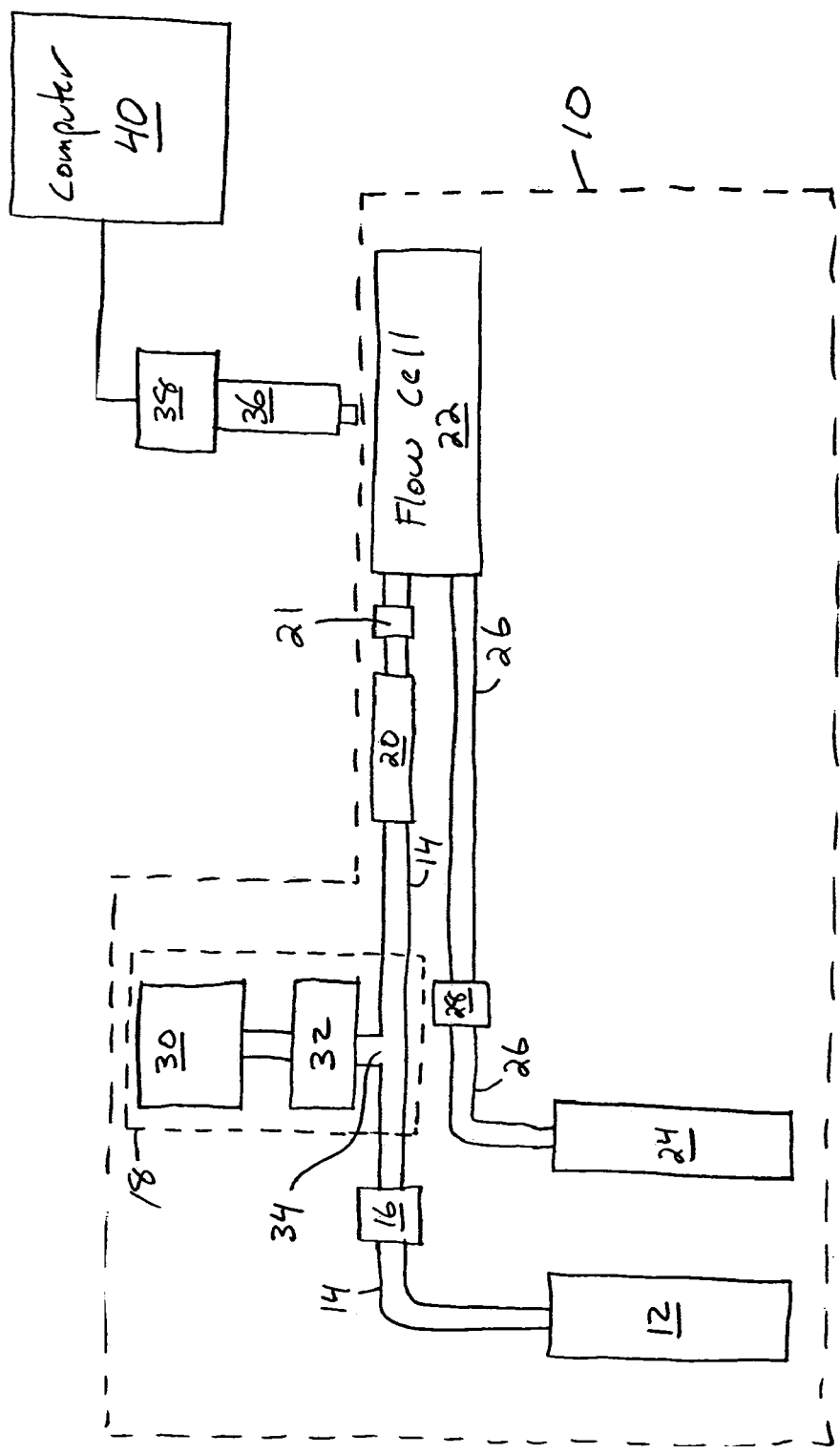
FIG. 1 is a plan diagram illustrating the particle analyzer fluid processing subsystem of the present invention.

The in-line fluid mixer and sensor of the present invention is graphically illustrated in FIG. 1 as part of the fluid processing subsystem 10 of a particle analyzer device of the type described above (e.g. see U.S. Pat. Nos. 4,338,024 and 4,393,466, which have been incorporated herein by reference).

The fluid processing subsystem 10 includes a specimen collection device 12, a specimen delivery tube 14, a specimen fluid pump 16, a stain injection device 18, an in-line mixer 20, a fluid sensor 21, and a flow cell 22. Subsystem 10 also includes a sheath fluid collection device 24, a sheath delivery tube 26, and a sheath fluid pump 28.

The specimen collection device 12 can be any conventional device used to introduce specimen (sample) fluid into the specimen delivery tube 14 (e.g. as simple as placing the input end of tube 14 in a container of the specimen, to as complex as a robotic pipetter that is dipped into one of a plurality of test tubes containing specimens to be examined). Delivery tube 14 is a hollow tube, with a small inner diameter (ID) to minimize the amount of specimen needed to operate flow cell 22. For example, ⅟₃₂-inch ID Teflon tubing can be used for delivery tube 14. Delivery tube 14 need not be a single continuous length of tubing, but could be several sections of tubing connected together, which components such as pump 16, mixer 20, etc. disposed between the tubing sections. Pump 16 can be any conventional pump (e.g. a peristaltic type pump) that draws the specimen fluid into and along specimen delivery tube 14. As a non-limiting example, about 800 μl of specimen can be aspirated from a specimen test tube over a 13.5 second period. With a ⅟₃₂ inch inner diameter (i.e. a cross-sectional area of only $4.95 \times 10^{-3}$ cm$^2$), a nominal linear velocity of specimen need to operate a conventional flow cell would be about 12 cm/sec. This amount of specimen fluid requires about 4.8 μl of stain, resulting in a stain deliver rate of about 360 nl/sec.

The stain injection device 18 includes a container of stain 30 and a dispensing valve 32 that injects predetermined quantities of the stain into the specimen fluid flowing along tube 14 (preferably using a tee connection 34). For the purposes of this disclosure, stain 30 can be any fluid usable to treat, react with, dye or stain the specimen fluid. The dispensing valve 32 injects controlled bolus volumes of stain (e.g. between about 10 nl to 100 nl per valve actuation impulse). It is expected that valve 32 would be activated at a rate of 3 to 12 impulses per second, with each impulse itself lasting less than about 2 msec. Depending on the impulse rates, the time between boluses can represent a "large" distance (as measured in specimen delivery tube diameters) along the specimen delivery tube 14. At 12 impulses per second, the distance between boluses is about 1 cm (about 12 diameters). However, at 3.6 impulses per second, this distance opens up to 42 diameters. These boluses of stain must be mixed with the linearly dispersed unstained specimen fluid disposed between boluses. The stain injected from the branch-arm of tee connection 34 into tube 14 tends to hug one wall of the tube 14 after injection, making mixing that much harder. Because the flow in tube 14 is laminar, there is very little natural mixing as the specimen (now with stain flowing along the wall) moves down tube 14. An in-line mixer 20 is therefore disposed along tube 14 after the point where the stain is injected, which thoroughly mixes the stain and the specimen fluid. By the time the specimen reaches the flow cell 22, the specimen is already well mixed with the stain.

The flow cell 22 can be any conventional flow cell design, and preferably utilizes sheath fluid (supplied by the sheath fluid collection device 24, the sheath delivery tube 26, and the sheath fluid pump 28, which are conventional and not discussed in any further detail) to buffer the specimen fluid into a small cross sectional examination area or region. A microscope 36 and digital camera 38 form an imager that captures images of the stained specimen fluid flowing through the flow cell 22, which are then analyzed using a computer 40 employing conventional particle identification techniques.

Figure 2A:
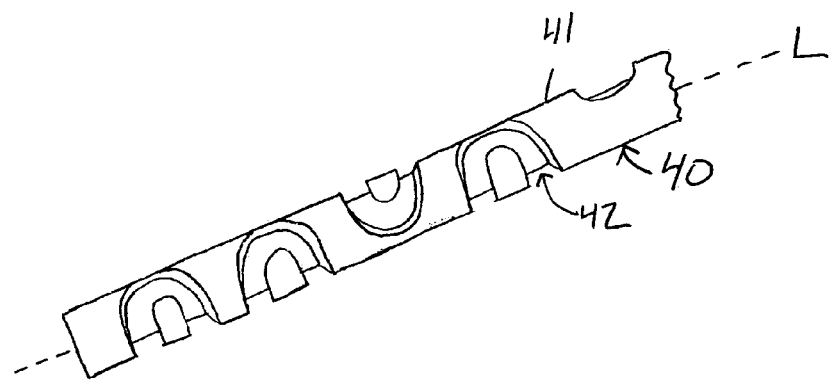
FIG. 2A is a side view of the in-line mixer cylindrical form of the present invention.
Figure 2C:
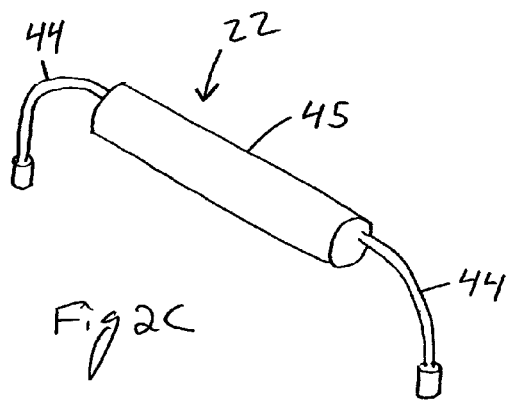
FIG. 2C is a perspective view of the in-line mixer of the present invention.
Figure 2B:
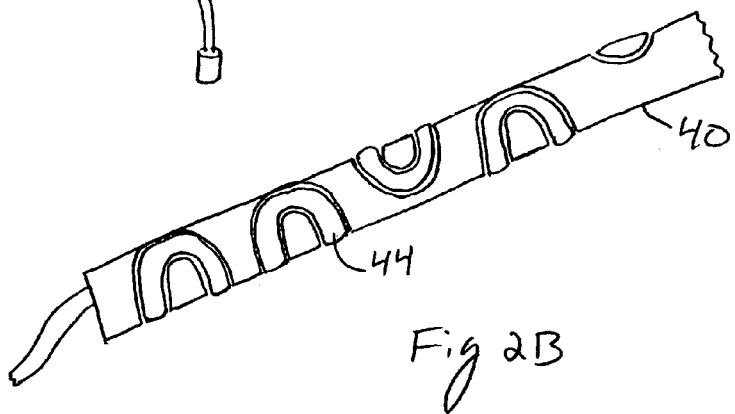
FIG. 2B is a side view of the in-line mixer cylindrical form of the present invention, with the mixer tube inserted in the cylindrical form channel.

The in-line mixer 20 of the present invention is shown in more detail in FIGS. 2A–2C, and includes an elongated core member 40 (having a longitudinal axis L), a continuous channel 42 formed into the outer surface 41 of core member 40, and a mixing tube 44 disposed in and along channel 42. The channel 42 defines a meandering fluid path that includes a plurality of three dimensional tight-radius turns in multiple directions in a relatively short physical length for both the mixing tube 44 and the in-line mixer 20 itself. A sheath 45 can be placed over the core member 40 to hold mixing tube 44 in channel 42. If sheath 45 is made of a clear material (e.g. clear plastic), then liquid flow through mixing tube 44 can be viewed during the mixing operation.

The present invention employs a fluid path that includes both radial and axial mixing turns. A radial mixing turn is one in which the direction vector of the flowing fluid is constantly changing so the fluid flows around the longitudinal axis L of the core member 40. It is mainly the outermost wall of the fluid path that implements a radial mixing turn (by forcing the fluid to turn about axis L). An axial mixing turn is one where the velocity component of the fluid in the direction parallel to the core member's longitudinal axis L is changed. It is mainly the side wall (between the outmost and innermost walls) of the fluid path that implements an axial mixing turn (by forcing the fluid to turn toward or away from one of the ends of axis L). Radial and axial turns can overlap, meaning that a single section of fluid path can include both radial and axial mixing turn components. In fact, axial mixing turns change the relative amount of fluid movement that is radial around the core member 40 (about axis L). Axial mixing turns are used to transition from a radial mixing turn in one direction to either no radial mixing turn or a radial mixing turn in the opposite direction. By forming the fluid path on the outer surface 41 of the core member 40, radial and axial mixing turns are combined, which prevents the fluid from flowing along one particular wall of the fluid path for too long a time.

There are several important considerations in determining the dimensions and locations of the fluid path radial and axial mixing turns. As fluid flows through a straight section of pipe (assuming a round cross-section), the maximum axial flow (i.e. flow down the center of the pipe) can be found at the pipe centerline. However, in a continuously curved pipe, the maximum axial flow is displaced outward from the pipe centerline, where the fluid driven outward across the core of the pipe flow forms a secondary flow in the radial plane as this fluid returns back along the pipe walls. (See Applied Fluid Dynamics Handbook, Van Nostrand Reinhold Col., Inc., New York, 1984, pp. 65–71, which is incorporated herein by reference). It is this secondary flow that creates the mixing effect for the fluid path. The secondary flow is a function of the Dean number DN, which is calculated as:

$$DN = (U \cdot D/v)(D/2 \cdot R)^{1/2} \quad (1)$$

where U is the average flow velocity over the pipe's cross-section, D is the pipe diameter, v is the kinematic viscosity of the fluid, and R is the radius of curvature of the pipe turn (i.e. measured from the pipe's centerline). Kinematic viscosity v is fluid viscosity (μ) divided by fluid density (ρ).

The term (U·D/v) is also known as the Reynolds number. As the Dean number for a curved pipe exceeds 10, the amount of secondary flow becomes significant for mixing purposes (see page 66 of the Applied Fluid Dynamics Handbook). Therefore, for efficient mixing, the curved portions of the fluid path need to have a small enough radius of curvature R, along with a sufficient fluid velocity, to produce a Dean number of at least 10. It should be noted that by simply reducing the flow velocity of an operating flow system to result in a Dean number of less than 10, effective mixing can be "disabled" without physically modifying the fluid path, which can be an important feature for some applications.

There are, however, several limitations on the minimum fluid path radius of curvature R that can be employed. First, if the radius of curvature R is too small, kinks can form in the tubing 44, which would significantly affect the passage area of the mixing tube 44 as well as providing ledges or crannies wherein carryover components could lurk. Second, if the ratio of R/D drops below about 2, then turbulent flow results which causes the formation of a low-pressure eddy about the inner radius of the bend (see page 67 of the Applied Fluid Dynamics Handbook). Such eddy systems would inhibit efficient mixing, and would provide a location for specimen fluid to get trapped in the mixing tube. Therefore, for efficient mixing, the curved portions of the fluid path need to have a large enough radius of curvature R to produce a ratio R/D of at least 2.

As a non-limiting example, the in-line mixer 20 of the present invention has been reduced to practice, using a Teflon, 1/32 inch ID, 1/16 inch outer diameter (OD) tube as mixing tube 44. Core member 40 is cylindrically shaped, with an OD of 0.250 inch, and is made of machined aluminum. The depth of channel 42 should be at least as great as the OD of the mixing tube 44, so tube 44 can be fully contained by channel 42. In this exemplary embodiment, the channel 42 is 0.070 inch wide and 0.070 inch deep, so that the maximum diameter of mixing tube 44, even when slightly distorted due to it's bending, still rests fully within the channel 42. After the mixing tube 44 is laid into the channel 42, the outer sheath 45 (0.250 inch ID) is slipped over the entire core member 40.

By design, the 0.250 inch OD aluminum core member 40 with the 0.070 inch deep channel 42 means that the center of the mixing tube 44 is wrapping around the core member 40 (i.e. radial mixing turns) with a nominal 0.090 inch radius of curvature (as measured from the center of the mixing tube 44). Moreover, as the channel 42 turns down the length of core member 40 (i.e. axial mixing turns), its center does so with 0.090 inch radius of curvature. Therefore, the three dimensional mixing turns made by the mixing tube 44 are rather complex, because as each mixing turn progresses, the mixing tube 44 moves both down and around core member 40, and therefore is changing its direction vector in two planes simultaneously. The net result is a very complex tubing path that undergoes multiple three-dimensional mixing turns that provide excellent fluid mixing in short tubing distances. The 0.090 axial and radial mixing turns provide sufficient mixing without forming eddy currents or tube kinks, providing the proper fluid stream velocity is used.

For the embodiment reduced to practice and described above, a fluid velocity U of 12 cm per second was used. The major component of the urine specimen is water, which as a kinematic viscosity of about $1 \times 10^{-6}$ m²/sec. Using equation 1, with a pipe diameter D of 0.03 inches (0.076 cm), and a radius of curvature of 0.09 inches (0.23 cm) for each of the mixing turns, the Dean number is calculated to be about 39, which is well above the value of 10 necessary for effective mixing. In addition, the ratio of R/D is 3, well above the minimum value of 2 needed to avoid turbulent flow and low-pressure eddies.

Figure 3:
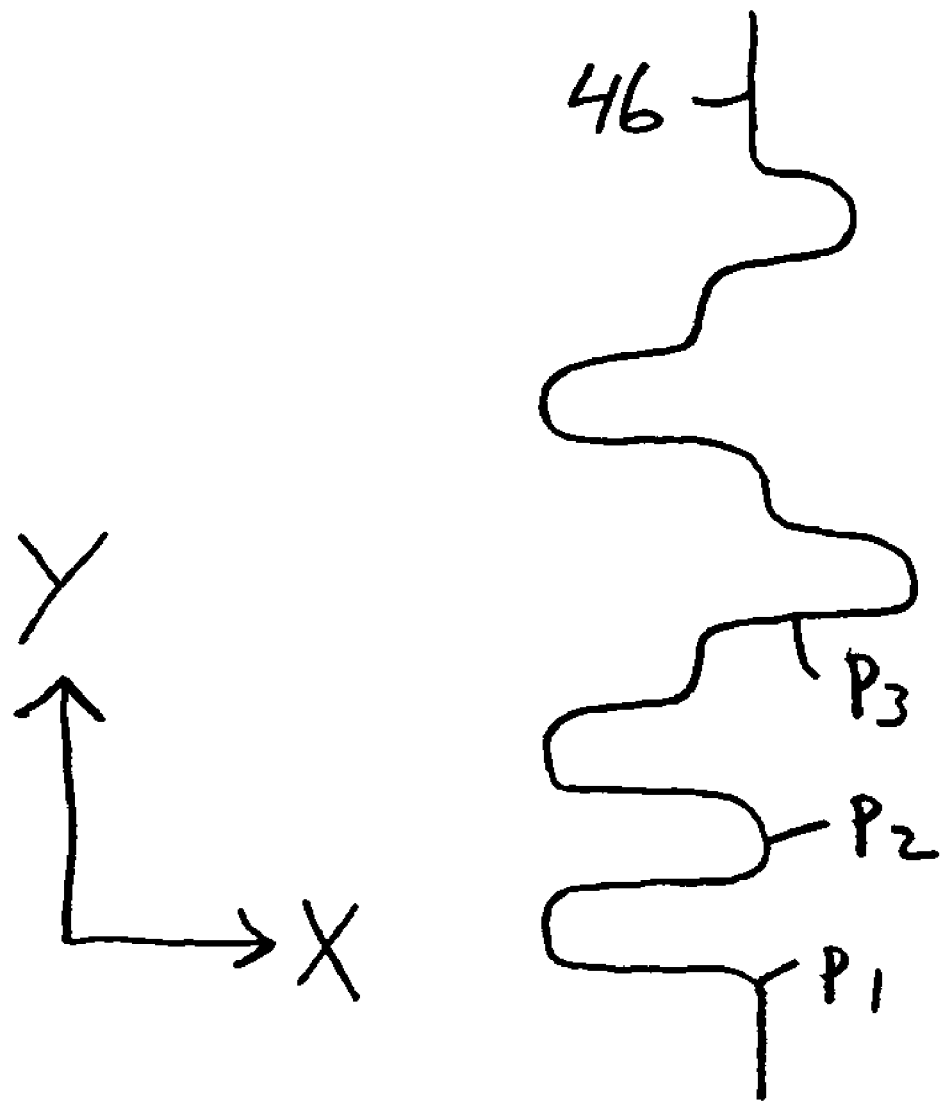
FIG. 3 is a diagram illustrating the turn schedule of the in-line mixer of the present invention.

The schedule of mixing turns down and around the core member 40 are preferably chosen to result in a varied set of mixing turn types, not necessarily random, but certainly meandering. The mixing turn schedule 46 for the embodiment illustrated in FIGS. 2A–2B is illustrated in a planar manner in FIG. 3, where movement "down" the core member 40 (along its length parallel to axis L) is in the vertical "Y" direction, and movement "around" the circumference of the core member 40 (about axis L) is in the horizontal "X" direction. Radial mixing turns are found anywhere on channel 42 where that portion of its mixing turn schedule 46 has any movement component in the X direction of FIG. 3, and axial mixing turns are found anywhere on channel 42 where its mixing turn schedule 46 represented in FIG. 3 is non-linear. Thus, for the mixing turn schedule 46 of FIG. 3, portion $P_1$ represents a 90 degree axial mixing turn, portion $P_2$ represents a 180 degree axial mixing turn, and portion $P_3$ represents a radial mixing turn, of the channel 42.

The three dimensional mixing turn schedule of the channel 42 is simply the flat mixing turn schedule 46 wrapped around the cylindrical core member 40, and cut into its outer surface with a width and depth of 0.070 inches. The axial and radial mixing turns can be directly connected, or separated by sections of channel 42 that do not contain axial and/or radial mixing turns. For the purposes of this disclosure, the beginning of any linear portion of mixing turn schedule 46, or any inflection point where the direction of rotation of the mixing turn (i.e. clockwise, counterclockwise) changes from one to the other, demarks the end(s) of the adjacent axial mixing turn(s). Likewise, any point along mixing turn schedule 46 that changes from a positive X direction component to a zero or negative X direction component, or vice versa, demarks the end(s) of the adjacent radial mixing turn(s). Thus, as illustrated in FIG. 3, the channel 42 having mixing turn schedule 46 includes six 180 degree axial mixing turns (three clockwise, three counterclockwise), and eight 90 degree axial mixing turns (four clockwise, four counterclockwise), all with the same radius of curvature: 0.090 inch nominally at the tube's center. Most portions of channel 42 also have at least some component of radial mixing turning.

The exemplary channel 42 illustrated in FIGS. 2A–2B includes portions where the radial mixing turns overlap with axial mixing turns (fluid turning both axially and radially), portions of radial mixing turns that do not overlap with any axial mixing turns (fluid turning radially only), and portions containing no mixing turns at all (fluid undergoing no turning—moving parallel to axis L). Intermixing axial mixing turns of different degrees of rotation (e.g. 90 and 180 degrees) and different directions of rotation (e.g. clockwise and counterclockwise), together with radial mixing turns of different directions (clockwise and counterclockwise about axis L), increases the mixing efficiency of the in-line mixer 20. Of course, the placement and number of each type of mixing turn, as well as the actual number of degrees of rotation of each mixing turn, can vary, and are not limited to the order and actual degrees of rotation of the axial/radial mixing turns illustrated in the figures.

The core member 40 with channel 42 can be made on an NC milling machine with rotation based on the left-right dimensions, and "down" the tube as a linear control. A numerical database can be used to provide incremental moves for the milling machine so that each 90-degree turn is represented by a plurality (e.g. 16) points. The data points are the delta-moves from the previous point, and each data point is described by a "Y" (linear) value, and an "A" (angular) value.

The exemplary in-line mixer 20 described above is 2 inches long, and 0.375 inches in diameter (OD of the external sheath 45). Yet, the "effective" tube length (i.e. the linear length of channel 42) is 4.81 inch. The length of mixing tube 44 used is longer than the effective tube length of channel 42, so that the ends of mixing tube 44 extend beyond the ends of in-line mixer 20 for connection to delivery tube 14. It should be noted that winding the mixing tube 44 through channel 42 has been found to reduce the volume of that portion of mixing tube 44 (e.g. by about 22%), further reducing the amount of fluid contained in the in-line mixer 20. The volume reduction is an indication of the distortion of the tubing by the winding schedule.

The in-line mixer 20 of the present invention incorporates a low-tech, low-cost solution in a novel arrangement, whereby a continuous mixing tube is used, with no "nooks or crannies" to store specimen residue. The mixing tube 44 is bent in smooth, limited radius mixing turns that avoid kinks or places in the tube where contaminants can "lurk." Further, by utilizing minimum radius mixing turns, the washing or rinsing process not only gets to all of the tube's inner surface areas as easily as was done by the specimen fluid during the mixing process, but also the rinsing fluid is effectively mixed as well (assuming the viscosity and velocity of the rinsing fluid produces a Dean number of at least 10) thus enhancing the effectiveness of the rinse cycle. To rinse the system, the specimen fluid in the collection device 12 can be replaced by a rinsing fluid, or the rinsing fluid can otherwise be injected into specimen fluid delivery tube and pumped by pump 16 or by a separate rinse fluid pump.

By laying tubing in a channel machined along the surface of a cylinder having a defined diameter guarantees that the desired minimum radiuses are maintained. The random wandering of the flow direction vector of the fluid flow path enhances the overall mixing process, with flow lines that shift from one wall of the tube to another. Without the random wandering, (as in the case of a helical coil mixer) the flowing liquids along a particular wall tend to run along the same wall, and never really mix with liquid parts on some other wall. Using clear materials for the outer sheath 45 and the mixing tube 44 allows the user to view the mixing process, and to ensure the mixing tube 44 was inserted in the channel 42 without kinking. It may even be possible to heat the mixing tube 44 while in the channel 42, so that when the assembly cools, the formed mixing tube 44 can be extracted from the assembly, where it will hold the form it had when it was in the channel 42. The in-line mixer 20 mixes the specimen fluid in a small volume to minimize the amount of specimen needed and in a relatively short length to minimize the transit time along the mixing path.

The in-line mixer 20 of the present invention is also compatible with any flow cells that may not be able to accommodate a great enough fluid flow during flow cell operation for adequate concurrent mixing. For example, if flow cell 22 needs to operate at a fluid flow rate that generates just 1.2 cm/sec fluid velocity through the in-line mixer 20 described above, then a Dean number of just 3.9 results, which is inadequate for proper mixing. In such a case, the system can be modified in the following way to provide adequate mixing. First, the portion of delivery tubing 14 between the in-line mixer 20 and the flow cell 22 is made long enough to have a volume sufficient to contain enough of the mixed specimen fluid to operate the flow cell at its optimum flow rate. Second, pump 16 is set to pump specimen fluid at two flow rates: a first flow rate which is sufficient for mixing the specimen fluid in the in-line mixer 20 with a Dean number of at least 10 (and for sufficiently filling the tubing portion between the in-mixer 20 and flow cell 22 with the adequately mixed specimen fluid), and a second (lower) flow rate for operating the flow cell 22 with the adequately mixed specimen fluid contained in the tubing. With this configuration, data acquisition by the imager from the flow cell 22 is completed before the adequately mixed specimen fluid is exhausted, and before any of the specimen fluid that travels through the in-line mixer at the second (lower) flow rate reaches the flow cell 22. Thus, mixing specimen fluid with a Dean number of at least 10 need not be concurrent with flow cell operation with that mixed specimen fluid.

Figure 4:
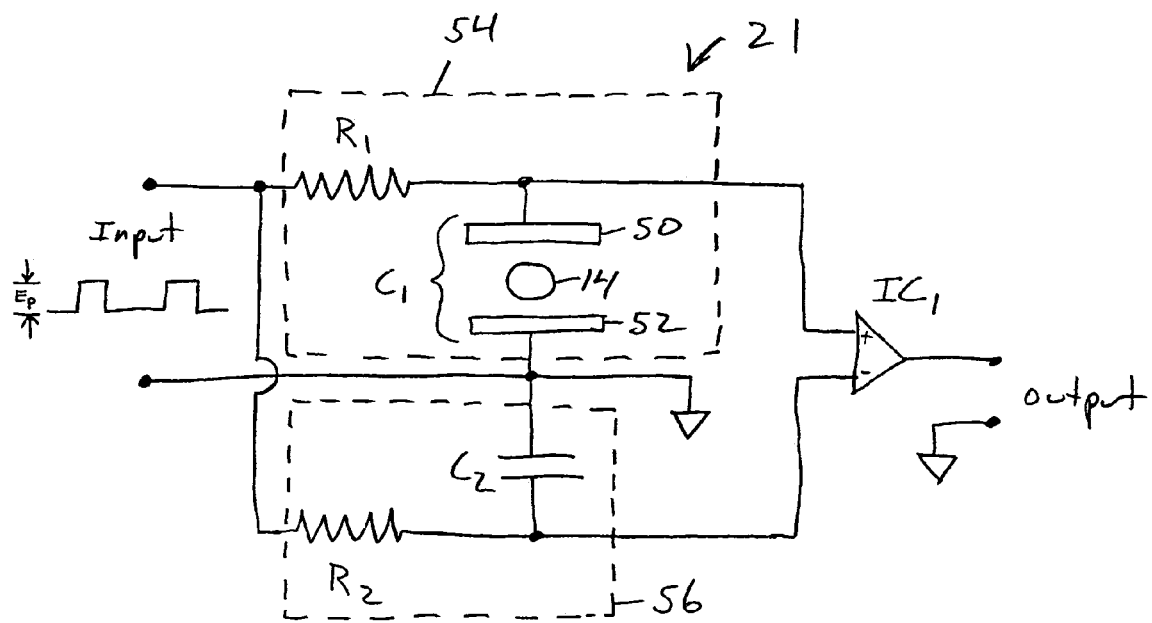
FIG. 4 is a schematic diagram of the in-line fluid sensor of the present invention.

FIG. 4 illustrates the components of the fluid sensor 21, which detects the presence of fluid in delivery tube 14. Sensor 21 can sense the very small capacitance change for electrodes outside of delivery tube 14 caused by the presence or absence of a water-based liquid inside tube 14. Sensor 21 includes a pair of electrodes 50 and 52 with delivery tube 14 disposed therebetween. At least that portion of delivery tube 14 disposed between electrodes 50/52 should be made of relatively low dielectric material (e.g. plastic or glass), and not metal. The electrodes 50/52 can be small parallel plates with the delivery tube 14 sandwiched in between. Alternately, electrodes 50/52 can be cascaded tight-fitting metal tubes surrounding the fluid-carrying tube 14. Electrode 52 is connected to ground potential, while electrode 50 is the delivery tube capacitance sensing electrode. Sensing electrode 50 has a capacitance relative to the ground electrode 52, even in the absence of any water in tube 14. This residual capacitance can be in the order of 5 to 20 times the actual change in capacitance due to the presence or absence of water between electrodes 50/52. Thus, one of the big challenges is to stably detect changes in the base capacitance.

Sensor 21 uses an oscillating voltage signal to drive a resistor $R_1$, that is connected to sensing electrode 50 (which has a base capacitance $C_1$ to ground). The oscillating signal shown in FIG. 4 is a square-wave, but other oscillating types signals could be used instead. Resistor $R_1$ and electrodes 50/52 form a first RC circuit 54, having an output that is connected to the input of a high speed comparator $IC_1$. The higher that $C_1$ is, the larger the time constant, $\tau(\tau=R_1 C_1)$ of the exponential signal that would be observed at the input of $IC_1$. The best time t for comparing a rising exponential is at $t/\tau=1.00$, that is, at one time constant. Thus, the sensor 21 could simply measure the capacitance $C_1$ by measuring the instantaneous voltage of sensor plate 50 at a time $t=R_1C_1$, and comparing this voltage to a reference voltage corresponding to $0.632 \cdot E_p$, where $E_p$ is the amplitude of the square wave driving the $R_1C_1$ circuit 54. However, the comparator $IC_1$ itself has some capacitance on its input node, and this capacitance can change with temperature, and time. Since sensor 21 measures the presence/absence of fluid with a capacitance change of only a few tenths of a picoFarad, a measuring circuit with temperature drifts on the order of many tenths of a picoFarad will mask the real change that is being detected.

Therefore, sensor 21 includes a second RC circuit 56, with a resistor $R_2$ driven by the same oscillating (square-wave) signal as is resistor $R_1$, and a capacitor $C_2$ also connected between $R_2$ and ground potential. The output of second RC circuit 56 provides a reference signal, which is applied to the reference side of the high speed comparator $IC_1$. The $R_2C_2$ time constant of the second RC circuit 56 is chosen to be the same as that of the sensing electrode 50 at the capacitance level at the decision threshold. The magnitude of the difference between two similar exponentials is a maximum around one time constant. If the capacitance $C_1$ of the sense electrode 50 is larger than the "equal" time constant value, its exponential will rise slower than that of the second RC circuit 56, and the voltage of sense electrode 50 at the one time constant would be somewhat lower than that of the reference signal. If the capacitance $C_1$ of the sense electrode 50 is less than the "equal" time constant value, its exponential would rise faster than that of the second RC circuit 56, and the voltage of sense electrode 50 at the one time constant would be higher than that of the reference signal. A "strobe" comparator output at approximately one time constant is used, and the strobed output is stored as the "liquid" or "air" decision.

Sensor 21 has a self-tracking capability, where the drift in capacitance of the two comparator inputs track each other. Similarly, since both comparator inputs are the result of the same square wave drive, changes in the square wave signal amplitude do not adversely affect the sensor's results. The time constants should initially be nulled at the decision point, so that from then on the reference voltage accurately tracks drifts in the sensor electrode voltage (to a first order approximation). When one time constant is greater than the other, there will be a finite (and measurable or comparable) difference in the values at approximately one time constant, and that difference can be detected. Because the sensor strobes in the near vicinity of one time constant, and reasonable values of sense electrode capacitance and drive resistance put the nominal time constant on the order of about 100 nsec, the comparator $IC_1$ should have a response time that is very small compared to 100 nsec. The square wave drive can be provided by a 74ACxx device—that gives nice, low impedance drive levels. The strobing can be done by placing the output of comparator $IC_1$ on the D-input of a 74AC74 device, and a rising clock edge delayed 100 nsec after the driving square wave signal.

It is to be understood that the present invention is not limited to the embodiment(s) described above and illustrated herein, but encompasses any and all variations falling within the scope of the appended claims. For example, the core member need not have a cylindrical outer surface shape, but instead can have any shape (e.g. elliptical, square, etc.) that satisfies the criteria set forth above for efficient, low turbulence mixing. The mixing tubing 44 can be omitted, and instead the specimen fluid can be flowed directly through channel 42, where sheath 45 or other material can be used to seal channel 42 and prevent fluid from leaking therefrom. Alternately, the core member can be omitted, where the mixing tubing is formed around an imaginary longitudinal axis and is rigid enough (e.g. through heating) by itself or by attachment to rigid material to maintain the mixing turns without being disposed inside the channel of a rigid core member. In addition to the mixing turns, other turns which are not efficient at mixing the specimen fluid could be added to the fluid path of the mixer, without necessarily compromising the in-line mixer of the present invention. Different portions of the fluid path through the mixer can have different diameters and thus different fluid velocities, and the various mixing turns need not have the same radius of curvature.

What is claimed is:

1. A fluid mixing device for mixing a fluid having a fluid kinematic viscosity $\nu$, comprising:
    a core member having an outer surface and a longitudinal axis; and a channel formed in the outer surface for receiving the fluid, wherein the channel includes at least one radial mixing turn and a plurality of axial mixing turns through which the fluid flows;

wherein the fluid flowing through the channel is mixed by the radial and axial mixing turns.

2. The fluid mixing device of claim 1, wherein the channel forms a fluid path that has a diameter D, and wherein for each of the radial and axial mixing turns, the fluid flows through the mixing turn with a velocity U and the mixing turn has a radius of curvature R such that $(U \cdot D/v)(D/2 \cdot R)^{1/2}$ is at least about 10.

3. The fluid mixing device of claim 2, wherein for each of the radial and axial mixing turns, the radius of curvature R thereof is at least $2 \cdot D$.

4. The fluid mixing device of claim 2, wherein the radial and axial mixing turns all have substantially the same radius of curvature R and substantially the same diameter D.

5. The fluid mixing device of claim 1, further comprising:
a hollow mixing tube disposed in the channel, wherein the mixing tube forms a fluid path that has a diameter D and traverses the radial and axial mixing turns, wherein for each of the radial and axial mixing turns, the fluid flows through the mixing turn with a velocity U and the mixing turn has a radius of curvature R such that $(U \cdot D/v)(D/2 \cdot R)^{1/2}$ is at least about 10.

6. The fluid mixing device of claim 5, wherein for each of the radial and axial mixing turns, the radius of curvature R thereof is at least $2 \cdot D$.

7. The fluid mixing device of claim 5, wherein the radial and axial mixing turns all have substantially the same radius of curvature R and substantially the same diameter D.

8. The fluid mixing device of claim 1, wherein the plurality of axial mixing turns includes at least two different degrees of rotation.

9. The fluid mixing device of claim 8, wherein the at least two different degrees of rotation include substantially 90 degrees and substantially 180 degrees.

10. The fluid mixing device of claim 1, wherein the plurality of axial mixing turns includes both clockwise and counterclockwise directions of rotation.

11. The fluid mixing device of claim 1, wherein the at least one radial mixing turn includes a plurality of radial mixing turns.

12. The fluid mixing device of claim 11, wherein the plurality of radial mixing turns includes both clockwise and counterclockwise directions of rotation.

13. The fluid mixing device of claim 11, wherein the channel includes:
first portions where one of the radial mixing turns and one of the axial mixing turns overlap each other, and
second portions each with one of the radial mixing turns but none of the axial mixing turns.

14. The fluid mixing device of claim 13, wherein the channel further includes:
third portions that are substantially linear.

15. A particle analyzer, comprising:
a source of specimen fluid;
a flow cell;
a mixing device that includes:
a core member having an outer surface and a longitudinal axis, and
a channel formed in the outer surface having at least one radial mixing turn and a plurality of axial mixing turns; and
a pump for pumping the specimen fluid from the specimen fluid source, through the mixing device wherein the specimen fluid flowing through the channel undergoes mixing by the radial and axial mixing turns, and then to the flow cell.

16. The particle analyzer of claim 15, further comprising:
a source of stain; and
a dispensing valve for injecting the stain from the stain source into the specimen fluid, wherein the stain and specimen fluid are mixed together by the mixing device.

17. The particle analyzer of claim 16, wherein:
the channel forms a fluid path that has a diameter D;
the specimen fluid has a fluid kinematic viscosity v; and
for each of the radial and axial mixing turns, the specimen fluid and stain flows through the mixing turn with a velocity U and the mixing turn has a radius of curvature R such that $(U \cdot D/v)(D/2 \cdot R)^{1/2}$ is at least about 10.

18. The particle analyzer of claim 17, wherein for each of the radial and axial mixing turns, the radius of curvature R thereof is at least $2 \cdot D$.

19. The particle analyzer of claim 17, wherein the radial and axial mixing turns all have substantially the same radius of curvature R and substantially the same diameter D.

20. The particle analyzer of claim 17, further comprising:
hollow tubing for conveying the specimen fluid from the mixing device to the flow cell;
wherein the specimen fluid pumped through the mixing device at the velocity U flows into the hollow tubing; and
wherein the pump then pumps specimen fluid from the specimen fluid source through the mixing device at a velocity X which is less than velocity U, where $(X \cdot D/v)(D/2 \cdot R)^{1/2}$ is less than about 10.

21. The particle analyzer of claim 20, wherein as the specimen fluid is pumped through the mixing device at the velocity X, the specimen fluid that flowed through the mixing device at the velocity U flows through the flow cell.

22. The particle analyzer of claim 20, further comprising:
an imager for capturing images of the specimen fluid flowing through the flow cell, wherein the imager captures images of the specimen fluid that flowed through the mixing device at velocity U, but ceases the capturing of images before the specimen fluid that flowed through the mixing device at velocity X reaches the flow cell.

23. The particle analyzer of claim 17, further comprising:
a source of rinsing fluid having a kinematic viscosity of $v_2$;
means for pumping the rinsing fluid through the radial and axial mixing turns with a velocity $U_2$ such that $(U_2 \cdot D/v_2)(D/2 \cdot R)^{1/2}$ is at least about 10.

24. The particle analyzer of claim 16, further comprising:
a hollow mixing tube disposed in the channel, wherein:
the mixing tube forms a fluid path that has a diameter D and traverses the radial and axial mixing turns,
the specimen fluid has a fluid kinematic viscosity v, and
for each of the radial and axial mixing turns, the fluid flows through the mixing turn with a velocity U and the mixing turn has a radius of curvature R such that $(U \cdot D/v)(D/2 \cdot R)^{1/2}$ is at least about 10.

25. The particle analyzer of claim 24, wherein for each of the radial and axial mixing turns, the radius of curvature R thereof is at least $2 \cdot D$.

26. The particle analyzer of claim 24, wherein the radial and axial mixing turns all have substantially the same radius of curvature R and substantially the same diameter D.

27. The particle analyzer of claim 16, wherein the channel includes:

first portions where one of the radial mixing turns and one of the axial mixing turns overlap each other, and second portions each with one of the radial mixing turns but none of the axial mixing turns.

28. The particle analyzer of claim 27, wherein the channel further includes:

third portions that are substantially linear.

29. The particle analyzer of claim 24, further comprising:

hollow tubing for conveying the specimen fluid from the mixing device to the flow cell;

wherein the specimen fluid pumped through the mixing device at the velocity U flows into the hollow tubing; and wherein the pump then pumps specimen fluid from the specimen fluid source through the mixing device at a velocity X which is less than velocity U, where $(X \cdot D/v)(D/2 \cdot R)^{1/2}$ is less than about 10.

30. The particle analyzer of claim 29, wherein as the specimen fluid is pumped through the mixing device at the velocity X, the specimen fluid that flowed through the mixing device at the velocity U flows through the flow cell.

31. The particle analyzer of claim 29, further comprising:

an imager for capturing images of the specimen fluid flowing through the flow cell, wherein the imager captures images of the specimen fluid that flowed through the mixing device at velocity U, but ceases the capturing of images before the specimen fluid that flowed through the mixing device at velocity X reaches the flow cell.

32. The particle analyzer of claim 15, wherein the plurality of axial mixing turns includes at least two different degrees of rotation.

33. The particle analyzer of claim 32, wherein the at least two different degrees of rotation include substantially 90 degrees and substantially 180 degrees.

34. The particle analyzer of claim 15, wherein the plurality of axial mixing turns includes both clockwise and counterclockwise directions of rotation.

35. The particle analyzer of claim 15, wherein the at least one radial mixing turn includes a plurality of radial mixing turns.

36. The particle analyzer of claim 35, wherein the plurality of radial mixing turns includes both clockwise and counterclockwise directions of rotation.

37. A fluid mixing device for mixing a fluid having a fluid kinematic viscosity v, comprising:

a hollow mixing tube disposed about a longitudinal axis for receiving the fluid, wherein the mixing tube forms a fluid path having at least one radial mixing turn and a plurality of axial mixing turns through which the fluid flows;

wherein the fluid flowing through the fluid path is mixed by the radial and axial mixing turns.

38. The fluid mixing device of claim 37, wherein the fluid path has a diameter D, and wherein for each of the radial and axial mixing turns, the fluid flows through the mixing turn with a velocity U and the mixing turn has a radius of curvature R such that $(U \cdot D/v)(D/2 \cdot R)^{1/2}$ is at least about 10.

39. The fluid mixing device of claim 38, wherein for each of the radial and axial mixing turns, the radius of curvature R thereof is at least $2 \cdot D$.

40. The fluid mixing device of claim 38, wherein the radial and axial mixing turns all have substantially the same radius of curvature R and substantially the same diameter D.

41. The fluid mixing device of claim 37, wherein the plurality of axial mixing turns includes at least two different degrees of rotation.

42. The fluid mixing device of claim 41, wherein the at least two different degrees of rotation include substantially 90 degrees and substantially 180 degrees.

43. The fluid mixing device of claim 37, wherein the plurality of axial mixing turns includes both clockwise and counterclockwise directions of rotation.

44. The fluid mixing device of claim 37, wherein the at least one radial mixing turn includes a plurality of radial mixing turns.

45. The fluid mixing device of claim 44, wherein the plurality of radial mixing turns includes both clockwise and counterclockwise directions of rotation.

46. The fluid mixing device of claim 44, wherein the mixing tube includes:

first portions where one of the radial mixing turns and one of the axial mixing turns overlap each other, and second portions each with one of the radial mixing turns but none of the axial mixing turns.

47. The fluid mixing device of claim 46, wherein the mixing tube further includes third portions that are substantially linear.

* * * * *